US00PP31628P2

(12) United States Plant Patent
Hansen

(10) Patent No.: US PP31,628 P2
(45) Date of Patent: Mar. 31, 2020

(54) **X *HANSARA* PLANT NAMED 'JUMPING JACKS'**

(50) Latin Name: **x *Hansara* hybrid**
Varietal Denomination: Jumping Jacks

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/501,209

(22) Filed: Mar. 6, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Hansara* plant named 'Jumping Jacks' characterized by compact habit and upright curving, lanceolate foliage with grayish-green color and in high ultra violet light exposure developing burgundy speckling on top and bottom. The leaf tips are narrowly acute without mucros. The marginal teeth are small and flexible. The plant produces yellowish flowers with orangish backs from orangish buds on tall stiff scapes are suitable as a potted plant or for the garden and loaded with nectar for attracting hummingbirds or for use as a houseplant.

2 Drawing Sheets

Botanical classification: x *Hansara* hybrid.
Variety denomination: 'Jumping Jacks'.

STATEMENT REGARDING PRIOR DISCLOSURES UNDER 37 CFR 1.77(b)(6)

The first public disclosure of the claimed plant, in the form of a private sale, was made by Walters Gardens, Inc. on Mar. 12, 2018 to Plant Delights Nursery, Inc. Plants for this sale were obtained from the inventor. This sale was followed by a non-enabling brief description on the website of Plant Delights Nursery, Inc. and also on the Walters Gardens, Inc. website. No plants of x *Hansara* 'Jumping Jacks' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Hansara* plant, x *Hansara* 'Jumping Jacks' hybridized on Nov. 5, 2014 by the inventor at a wholesale perennial nursery in Zeeland, Mich., USA as a cross between an unreleased proprietary trigeneric hybrid known by the breeder code HAN12-83-9 (not patented) as the female or seed parent and x *Mangave* 'Bloodspot' (not patented) as the male or pollen parent. Through trials at the same nursery the plant was referred to by the code xMANG 15-25-5. The new plant has been successfully asexually propagated initially in 2017 by division at the same nursery in Zeeland, Mich. and also by tissue culture. Both methods of asexual propagation systems have been found to produce stable and identical plants that maintain all the unique characteristics of the original plant in successive generations.

Following the International Code of Nomenclature for Cultivated Plants, Division III, Number 6, this first trigeneric hybrid is assigned the hybrid genus name of the original hybridizer' name and adding the "ara" ending to produce x *Hansara*. This is the first such hybrid known to the inventor between the three genera *Agave, Manfreda* and i Polianthes.

BRIEF SUMMARY OF THE INVENTION

X *Hansara* 'Jumping Jacks' differs from its parents as well as all other *Manfreda, Agave, Polianthes* and X *Mangave* known to the applicant. The most similar known cultivar known to the inventor are the x *Mangave* hybrids: 'Bloodspot' (not patented), 'Spotty Dotty' U.S. Plant Pat. No. 29,917, 'Inkblot' U.S. Plant Pat. No. 29,431, 'Bad Hair Day' U.S. Plant Pat. No. 30,279, 'Freckles and Speckles' U.S. Plant Pat. No. 30,904, 'Pineapple Express' U.S. Plant Pat. No. 28,613 and *Polianthes* x *bundrantii* 'Opal Eyes' (not patented).

'Spotty Dotty' has broader, more green leaves, with more spotting and more longitudinally folding in the leaf. 'Inkblot' has a more arching habit, the leaves arch more, with larger spots and a more greyed-purple coloration to the leaf and the flowers are burgundy-colored and not the yellowish flowers of 'Jumping Jacks'. 'Freckles and Speckles' has narrower foliage with more spotting and the flowers are yellowish-chartreuse from green buds on shorter stalks. 'Bad Hair Day' has more narrow foliage with much more arching habit and burgundy flowers. The male parent, 'Bloodspot', is more compact in habit, the leaves are shorter, thicker and more fibrous than the new plant. 'Pineapple Express' has taller scapes with chartreuse flowers and thicker leaves. *Polianthes* 'Opal Eyes' has fewer flowers that are narrow, more tubular and pinkish on the outside and burgundy on the inside. The foliage on 'Opal Eyes' is narrower and more flexible without marginal teeth. The female parent has bright yellow flowers on heavier branched scapes and the foliage is broader than the new plant. The male parent, 'Bloodspot', is more compact in habit, the leaves are shorter, thicker and more fibrous than the new plant.

The new plant, 'Jumping Jacks', is unique from all of these *Agave*, X *Mangave* and *Manfreda* known to the inventor by the following combined traits:

1. Compact habit with upright curved leaves;
2. Foliage lanceolate with small flexible marginal teeth;
3. Foliage develops burgundy speckling on top and bottom of glaucous green leaves;
4. Leaves are succulent and slightly fleshy;
5. Rapid growth rate;
6. Yellowish flowers from orangish buds on stiff, tall, lightly-branched scapes.

BRIEF DESCRIPTION OF THE DRAWINGS

The photograph of the new plant demonstrates the overall appearance of the new plant including the unique traits as a three-year-old plant grown in a container in a greenhouse with supplemental water and fertilizer and moved to a full-sun trial garden for summer growth. The colors are as accurate as reasonably possible with color reproductions. Ambient light spectrum, temperature, source and direction may cause the appearance of minor variation in color.

DETAILED BOTANICAL DESCRIPTION

Figure 1:
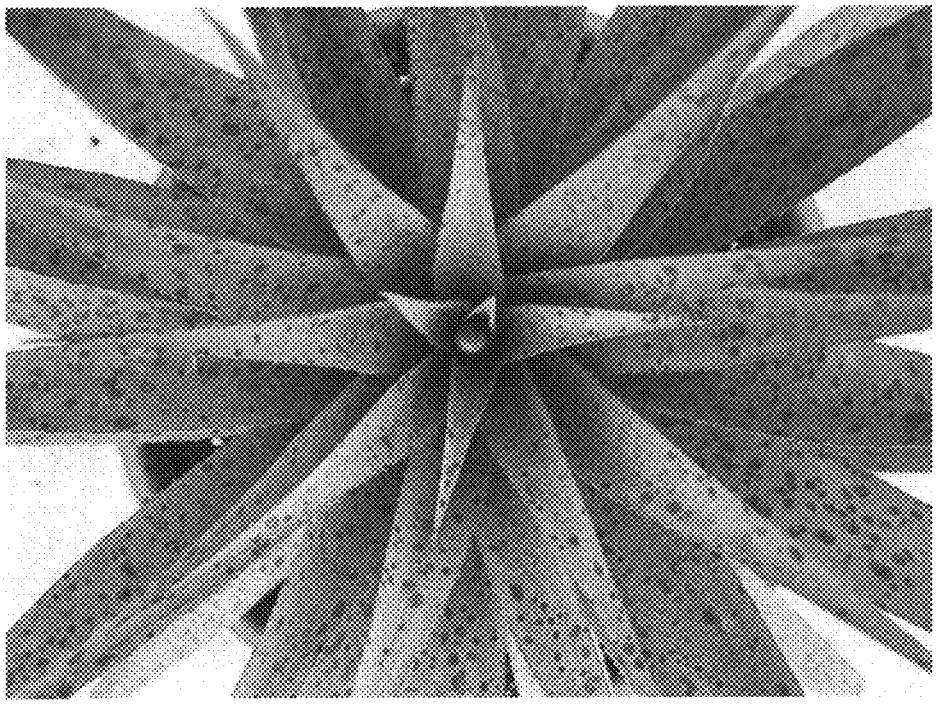
FIG. 1 shows the new plant in a container from above with a close-up of the foliage.
Figure 2:
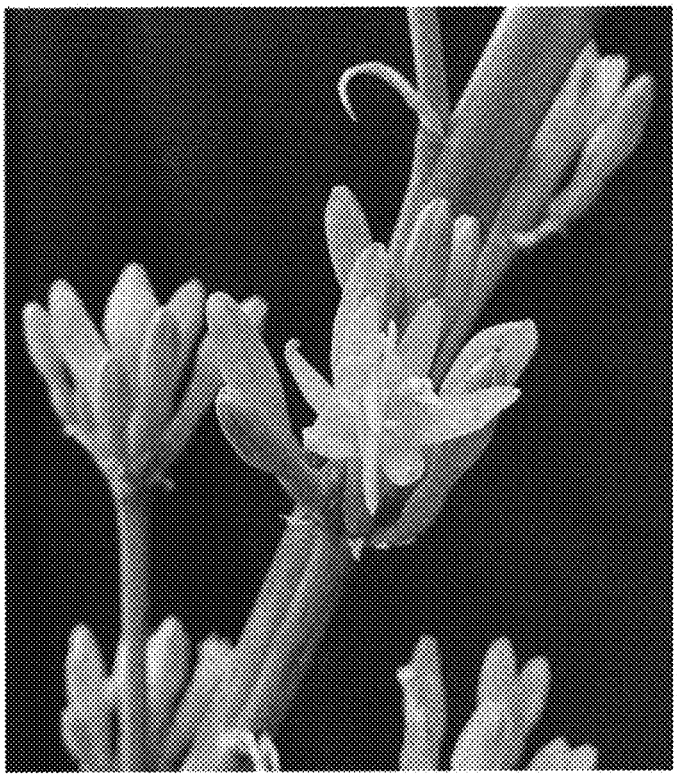
FIG. 2 shows a close-up of the flowers and buds in the upper scape.
Figure 3:
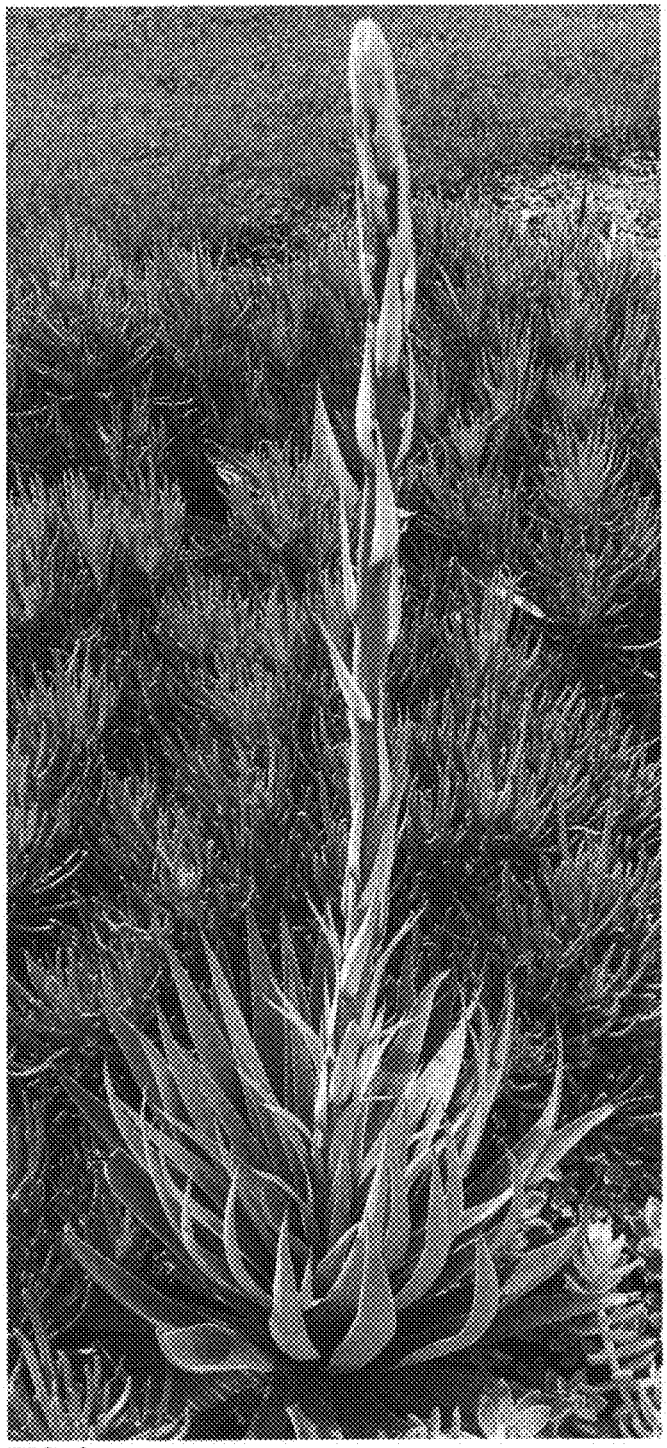
FIG. 3 shows the new plant with upright curving foliage and developing flower stalk.
Figure 4:
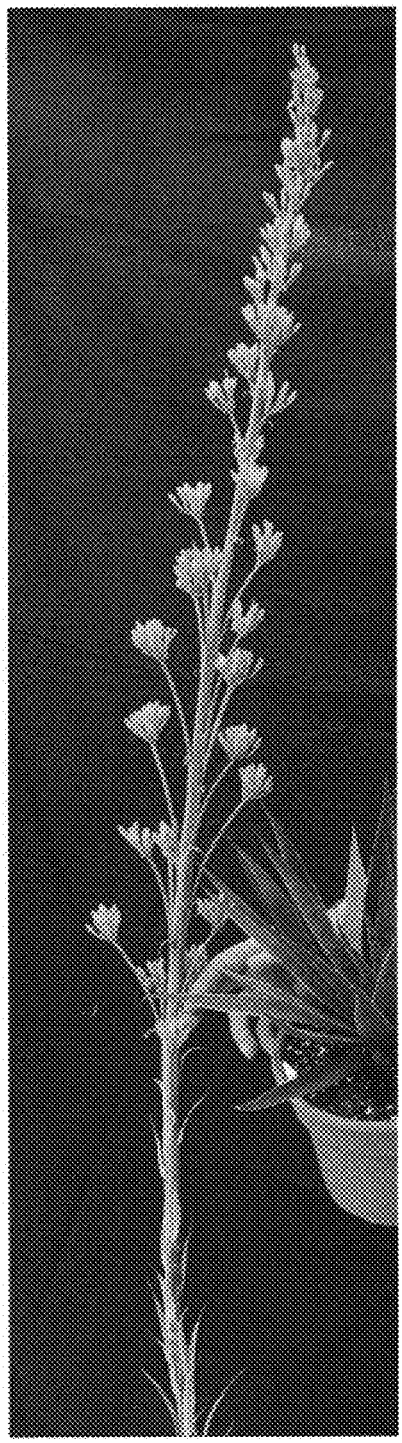
FIG. 4 shows the top portion of the scape with flowers and buds.

The following descriptions and color references are based on the 2015 edition of The Royal Horticultural Society Colour Chart except where common dictionary terms are used. The new plant, x *Hansara* 'Jumping Jacks', has not been observed under all possible environments. The phenotype may vary slightly with different environmental conditions, such as temperature, light, fertility, moisture and maturity levels, but without any change in the genotype. The following observations and size descriptions are of a three-year old plant in a commercial wholesale greenhouse and in a full-sun trial garden in Zeeland, Mich.

Parentage: HAN12-83-9 as the female or seed parent and x *Mangave* 'Bloodspot' as the male or pollen parent; HAN12-83-9 consists of a trigeneric hybrid with *Manfreda maculosa, Agave gypsophila* and *Polianthes* x *bundrantii* 'Opal Eyes';

Propagation: Division and sterile shoot tissue culture;

Time to initiate roots from tissue culture: About 21 days;

Growth rate: Rapid;

Crop time: About 12 to 14 weeks to finish during lengthening spring days from an established 25 mm tissue culture plug to a 65 mm diameter container;

Rooting habit: Fleshy and fibrous, with roots up to 15 cm long;

Root color: Nearest RHS 158C depending on soil type;

Plant shape and habit: Succulent herbaceous perennial with basal rosettes of up to about 112 fleshy leaves radially emerging and curving upwardly from central shortened stem, producing a symmetrical rounded mound;

Plant size: Foliage height about 30.0 cm tall from soil line to the top of the leaves, flowering to about 182.0 cm tall and about foliage to about 50.0 cm wide at the widest point above soil line;

Stem: To about 3.5 cm across; covered in leaves;

Foliage description: Lanceolate; simple; slightly fleshy; glaucous; glabrous; margins finely dentate with flexible teeth; narrowly apex acute with flexible tip; base truncate, sessile, clasping;

Leaf size: To about 35.5 cm long, about 30.0 mm wide at base and 3.5 mm thick, average about 31.0 cm long, 27.0 mm wide and 3.0 mm thick; usually bi-laterally symmetrical; glabrous and glaucous above and below; spots of variable sizes from about 0.5 mm diameter to about 6.0 mm long and 4.0 mm across;

Marginal teeth: Flexible; about 1.0 mm long and 1.5 mm across at base, about 6.0 mm apart; with an average of about three smaller teeth about 0.5 mm long and 0.5 mm across at base between larger teeth;

Foliage fragrance: None observed;

Leaf blade color:

*Adaxial* (*young*).—Between RHS 189B and RHS 189C with spots of nearest RHS N187B and thin marginal color of between RHS 187B and RHS 187C.

*Abaxial* (*young*).—Between RHS 189B and RHS 189C with spots of between RHS N187C and RHS N187B and thin marginal color of between RHS 187B and RHS 187C.

*Adaxial* (*mature*).—Nearest RHS N138C, maculate with spots of between RHS187B and RHS N187C.

*Abaxial* (*mature*).—Nearest RHS N138C, maculate with spots of nearest RHS 189A in lower ultraviolet light and nearest RHS 187B to blend between RHS N187 to RHS N187B with high ultraviolet light.

*Teeth*.—Larger and smaller teeth variable, both abaxial and adaxial nearest RHS N186C and blend between RHS 186D and RHS NN155B.

Apical spine: Absent;

Petiole: Sessile;

Veins: Parallel; not distinct;

Peduncle: Terete; glaucous; glabrous; stiff; strong; lightly branched; about 182.0 cm long and 18.0 mm diameter at base and 14.0 mm diameter below first flowers; flowering portion about 60.0 cm tall and about 13.0 cm across; about 40 branches to about 10.0 cm long and about 4.0 mm diameter at base; attitude main peduncle and branches upwards, erect;

Peduncle color: Basal portion below flowers densely maculate nearest RHS 187A with limited undertone showing of between RHS 146A and RHS 147B, flowering portion nearest RHS 147C;

Pedicel: Terete; glaucous; glabrous; stiff; strong; upright; average about 5.0 mm long and 2.5 mm diameter;

Pedicel color: Nearest RHS 147C;

Cauline leaves: About 40 per scape below flowers; lanceolate; simple; slightly fleshy; glaucous; glabrous; slightly recurved downward away from stalk; margins finely dentate with flexible larger and smaller teeth; apex narrowly acute; base truncate, sessile, clasping; proximally about 26.5 cm long and about 18.0 mm wide at base, decreasing distally; color adaxial and abaxial and teeth same as basal leaves;

Buds one day prior to opening: Elongated globose; about 3.1 cm long and about 6.0 mm across at mid-tepal, base about 3.0 mm diameter;

Bud color: Distal portion between RHS 168D and RHS 168C, basal portion nearest RHS 138C;

Flower description: Perfect, actinomorphic; about 4.0 cm long and opening to about 3.0 cm across; lasting about 3 to 4 days per flower; flowering period about three weeks in late winter in Michigan greenhouse; producing abundant nectar; approximately 230 flowers per scape; attitude mostly upright;

Flower fragrance: Not detectable;

Tepals: Six in two identical sets of three; glaucous abaxial and slightly lustrous adaxial; glabrous both adaxial and abaxial; acute apex and fused base; about 3.2 cm long, fused in basal 1.8 cm and about 5.0 mm wide at above fusion;

Tepal color: Adaxial outer and inner tepal set base between RHS 6D and RHS 6C with apical blushing nearest RHS 168B; abaxial outer and inner set base surrounding ovary nearest RHS 138B with central portion blend between RHS 145B and RHS 10A and distal portion nearest RHS N163B;

Androecium: Six;

*Filaments*.—Six; terete distally, slightly applanate base; stiff and straight; about 3.3 cm long and 1.0 mm diameter at base; color nearest RHS 10B.

*Anther*.—Dorsifixed; longitudinal; about 8.0 mm long and 2.0 mm diameter before opening; after dehiscence curving backward; color nearest RHS 6D.

*Pollen*.—Abundant; color nearest RHS 4D.

Gynoecium: Single;

*Style*.—4.5 cm long and 1.5 mm diameter at base; color between RHS 159B and RHS 159C.

*Stigma*.—Turbinate, apex tri-lobed; about 2.5 mm tall and 3.0 mm across top; color nearest RHS NN155B.

*Ovary*.—Inferior.

Fruit: Tri-valved, loculicidal, dehiscent capsule; ellipsoidal; apex rounded; base rounded; about 9.0 mm long and 8.0 mm across;

Fruit color: When developing nearest RHS 137B; seed was harvested prior to dehiscence;

Seed: Slightly flattened, near round; about 2.0 mm across 1.2 mm thick; color lustrous, nearest RHS 202A;

Disease resistance: x *Hansara* 'Jumping Jacks' has not been observed to be resistant or susceptible to diseases common to other x *Mangave, Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Hansara* plant named 'Jumping Jacks' as herein described and illustrated.

* * * * *